United States Patent [19]

Deghenghi

[11] Patent Number: 5,962,409

[45] Date of Patent: Oct. 5, 1999

[54] SOMATOSTATIN-ANALOGOUS CYCLIC PEPTIDES WITH INHIBITORY ACTIVITY ON GROWTH HORMONE

[76] Inventor: Romano Deghenghi, Chesaux-Dessus, 1264-St. Cergue, Switzerland

[21] Appl. No.: 08/983,363

[22] PCT Filed: Jul. 17, 1996

[86] PCT No.: PCT/EP96/03149

§ 371 Date: Jan. 14, 1998

§ 102(e) Date: Jan. 14, 1998

[87] PCT Pub. No.: WO97/05167

PCT Pub. Date: Feb. 13, 1997

[30] Foreign Application Priority Data

Jul. 28, 1995 [IT] Italy ................... MI95A1670

[51] Int. Cl.[6] .............. C07K 14/655; A61K 38/31
[52] U.S. Cl. ................. 514/11; 514/9; 530/311; 530/317
[58] Field of Search .................. 530/317, 311; 514/11, 9

[56] References Cited

U.S. PATENT DOCUMENTS 4,904,642  2/1990  Coy et al. ................. 514/11
5,480,870  1/1996  Keri et al. ................. 514/16

FOREIGN PATENT DOCUMENTS

| 203031 | 11/1986 | European Pat. Off. . |
| 214872 | 3/1987 | European Pat. Off. . |
| 505680 | 9/1992 | European Pat. Off. . |
| 91/18016 | 11/1991 | WIPO . |
| 9221283 | 12/1992 | WIPO . |

OTHER PUBLICATIONS

R.Z. Cai et al.. "Superactive Octapeptide Somatostatin Analogs Containing Tryptophan at Position 1"; Proceedings of the National Academy of Sciences of USA, vol. 84, Apr. 1987, Washington, US.; pp. 2502–2506.

*Primary Examiner*—Cecilia J. Tsang
*Attorney, Agent, or Firm*—Pennie & Edmonds

[57] ABSTRACT

Cyclic peptides of general formula (I), wherein the groups are as described in the disclosure, having inhibitory activity on growth hormone. The peptides of formula (I) have also anticancer activity.

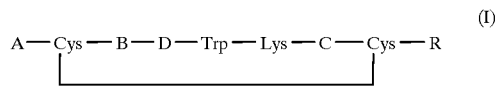

(I)

8 Claims, No Drawings

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: cyclic
      peptide
<220> FEATURE:
<221> NAME/KEY: SITE
<222> LOCATION: (1)
<223> OTHER INFORMATION: Xaa=D-2-Methyl-Trp
<220> FEATURE:
<221> NAME/KEY: SITE
<222> LOCATION: (4)
<223> OTHER INFORMATION: Xaa=D-Trp

<400> SEQUENCE: 1

Xaa Cys Tyr Xaa Lys Val Cys Thr
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: cyclic
      peptide
<220> FEATURE:
<221> NAME/KEY: SITE
<222> LOCATION: (1)
<223> OTHER INFORMATION: Xaa=D-betaNal
<220> FEATURE:
<221> NAME/KEY: SITE
<222> LOCATION: (4)
<223> OTHER INFORMATION: Xaa=D-Trp
<220> FEATURE:
<221> NAME/KEY: SITE
<222> LOCATION: (8)
<223> OTHER INFORMATION: Xaa=2-Methyl-Trp

<400> SEQUENCE: 2

Xaa Cys Tyr Xaa Lys Val Cys Xaa
 1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Description of Artificial Sequence: cyclic
      peptide
<220> FEATURE:
<221> NAME/KEY: SITE
<222> LOCATION: (1)
<223> OTHER INFORMATION: Xaa=D-2-Methyl-Trp
<220> FEATURE:
<221> NAME/KEY: SITE
<222> LOCATION: (4)
<223> OTHER INFORMATION: Xaa=D-Trp
<220> FEATURE:
<221> NAME/KEY: SITE
<222> LOCATION: (8)
<223> OTHER INFORMATION: Xaa=2-Methyl-Trp

<400> SEQUENCE: 3

Xaa Cys Phe Xaa Lys Val Cys Xaa
 1               5
```

SOMATOSTATIN-ANALOGOUS CYCLIC PEPTIDES WITH INHIBITORY ACTIVITY ON GROWTH HORMONE

TECHNICAL FIELD

The present invention relates to cyclic peptides which are homologues of somatostatin and have inhibitory activity on growth hormone.

BACKGROUND OF THE INVENTION

Somatostatin, or somatotropin-release inhibition factor, is a neuropeptide inhibiting the release of the growth hormone (somatotropin).

A number of somatostatin synthetic analogues are known, which are used in human and animal therapies.

In particular, octreotide has been known for some time, which is a somatostatin synthetic analogue used in therapy for the treatment of syndromes due to gastroenteral-pancreatic endocrine tumours, acromegaly as well as in the post-surgery treatment after pancreas surgery. Octreotide is also indicated as an agent inhibiting gastric secretion. This compound is described in U.S. Pat. No. 4,395,403 (Sandoz) and has the formula:

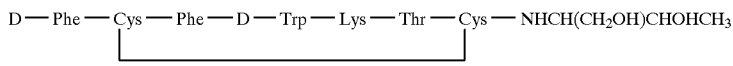

The octapeptide described above lies within a general formula of monocyclic polypeptides, comprising an hexapeptide residue containing a phenylalanine residue, optionally substituted at the 1-position of the aromatic ring, a cysteine residue at the 2-position, a D-trypthophan residue optionally substituted at the 4-position of the indole ring, a lysine residue at the 5-position, optionally N-alkylated at the position ε, an amino acid residue at the 6-position and a cysteine residue at the 7-position, the two sulfur atoms of the 2 and 7 cysteine residues are linked together and an amino acid residue at the 8-position.

Another somatostatin synthetic analogue, known under the name of Lanreotide, has been recently used in therapy. This compound has formula:

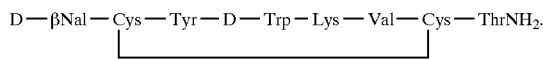

SUMMARY OF THE INVENTION

Now it has been found that compounds of formula (I)

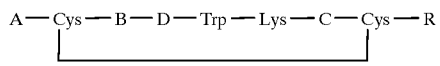

wherein

A is D-2AlkTrp, D-βNal, D-Phe;
B is Tyr, Phe;
C is Val, Thr;
R is ThrNH$_2$; 2AlkTrpNH$_2$ with the proviso that when A is D-βNal, B is not Tyr, C is not Val and R is not ThrNH$_2$ and the pharmaceutically acceptable salts of these peptides have activity inhibiting the release of the growth hormone and therefore are useful as active principles in human and animal medicine.

The present invention is based on the most surprising finding that the change of some structural characteristics, which had been defined essential in U.S. Pat. No. 4,395,403, not only keeps the somatostatin-like activity, but also shows further advantages in terms of specificity (see for example the expression of receptor sub-types in pituitary adenomas (G. M. Miller et al. J.C.E.M. 80, 1386, 1995) and in bronchial carcinoid tumors (H. Lefabre et al. J.C.E.M. 80, 1423, 1995).

DETAILED DISCLOSURE OF THE INVENTION

The abbreviations for the residues of amino acids therein used are in agreement with the standard nomenclature for the peptides, therefore, in the formula (I) reported above:

Cys=cysteine;

D-Trp=D-trypthophan;

Lys=L-lysine;

D-AlkTrp=D-2-alkyltryptophan;

D-β-Nal=D-β-naphthylalanine;

D-Phe=D-phenylalanine;

Tyr=L-tyrosine;

Phe=L-phenylalanine;

Val=L-valine;

Thr=L-threonine;

ThrNH$_2$=L-threonine amide

Alk TrpNH$_2$=L-2-alkyltryptophan amide.

According to the present invention, for alkyl at position 2- of the tryptophan residue it is intended that lower alkyl, comprising from 1 to 3 carbon atoms, be used. Examples of lower alkyl are methyl, ethyl, propyl, isopropyl. Among them, the methyl group is most preferred, and the abbreviation MeTrp is used to indicate 2-methyltryptophan.

All the three letter-abbreviations of the amino acids preceded by a "D" indicate the D-configuration of the amino acidic residue.

Preferred compounds according to the present invention are:

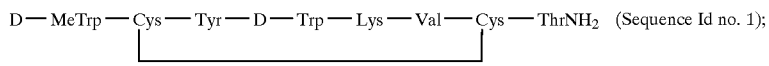 (Sequence Id no. 1);

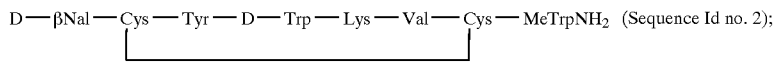 (Sequence Id no. 2);

-continued

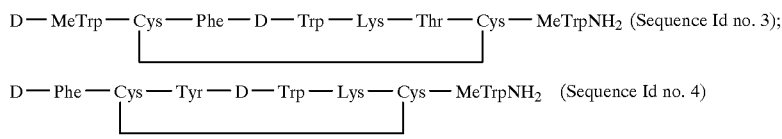

D—MeTrp—Cys—Phe—D—Trp—Lys—Thr—Cys—MeTrpNH₂ (Sequence Id no. 3);

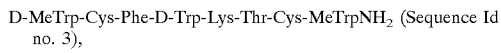

D—Phe—Cys—Tyr—D—Trp—Lys—Cys—MeTrpNH₂ (Sequence Id no. 4)

wherein MeTrp is 2-methyltryptophan.

The compound:

D-MeTrp-Cys-Phe-D-Trp-Lys-Thr-Cys-MeTrpNH₂ (Sequence Id no. 3), wherein MeTrp is 2-methyltryptophan, is most preferred.

The polypeptide compounds according to the present invention can be synthesized according to the usual methods of peptide chemistry, both solid-phase and solution, or by means of the classical methods known in the art. The solid-phase synthesis starts from C-terminal end of peptide. A suitable starting material can be prepared, for example attaching the required protected alpha-amino acid to a chloromethylated resin, a hydroxymethylated resin, a benzhydrylamine resin (BHA), or to a para-methylbenzhydrylamine resin (p-Me-BHA). As example, a chloromethylated resin is sold with the Trade Mark BIO-BEADS® SX 1 by BioRad Laboratories, Richmond, Calif. The preparation of the hydroxymethyl resin is described by Bodansky et al., Chem. Ind. (London) 38, 15997, (1966). The BHA resin is described by Pietta and Marshall, Chem. Comm., 650 (1970) and is commercially available by Peninsula Laboratories Inc., Belmont, Calif.

After the starting attachment, the protecting group of the alpha-amino acid can be removed by means of different acid reagents, comprising trifluoroacetic acid (TFA) or hydrochloric acid (HCl) dissolved in organic solvents at room temperature. After the removal of the protecting group of the alpha-amino acid, the remaining protected amino acids can be coupled step by step in the desired order. Each protected amino acid can generally be reacted in excess of about three times using a suitable carboxyl activating group, such as dicyclohexylcarbodiimide (DCC) or diisopropylcarbodiimide (DIC) dissolved, for example, in methylene chloride ($CH_2Cl_2$) or dimethylformamide (DMF) and their mixtures. After the desired amino acidic sequence has been completed, the desired peptide can be cleaved from the supporting resin by treatment with a reagent such as hydrogen fluoride (HF), which not only cleaves the peptide from the resin, but also the more common protecting groups of the lateral chains. When a chloromethylated resin or a hydroxymethylated resin is used, the treatment with HF leads to the formation of the acid peptide in free form. When a BHA or p-Me-BHA resin is used, the treatment with HF directly leads to the formation of the amide peptide in free form.

The above discussed solid-phase procedure is known in the art and was described by Atherton and Sheppard, Solid Phase Peptide Synthesis (IRL Press, Oxford, 1989).

Some methods in solution, which can be used to synthesize the peptide moieties of the present invention are detailed in Bodansky et al., Peptide Synthesis, 2nd edition, John Wiley & Sons, New York, N.Y. 1976 and in Jones, The Chemical Synthesis of Peptides, (Clarendon Press, Oxford, 1994).

These compounds can be administered to animals and humans at an effective dose which can be easily determined by the expert in the field and which can vary according to the specie, age, sex and weight of the treated subject. For example, in humans, when intravenously administered, the preferred dose falls in the range from about 0.1 μg to 10 μg of total peptide per kg of body weight. When orally administered, typically higher amounts are necessary. For example, in humans for the oral administration, the dosage level is typically from about 30 μg to about 1000 μg of polypeptide per kg of body weight. The exact level can be easily determined empirically based on the above disclosure.

Compositions comprising as active ingredient the organic and inorganic addition salts of the above described polypeptides and their combinations, optionally, in admixture with a vehicle, diluent, matrix or delayed release coating, are also comprised in the scope of the present invention. The delayed release pharmaceutical forms, comprising bioerodible matrixes suitable for subcutaneous implant, are particularly interesting. Examples of these matrices are described in WO9222600 and WO9512629.

The biological activity of the peptides according to the present invention has been evaluated in vitro and in vivo.

The study of the binding of the peptides on somatostatin receptors has been carried out according to the displacement method which consists in replacing from the receptors the radioligand (11-Tyr radioiodinated somatostatin 14-) before electrophoretic analysis on a denaturant polyacrylaminde gel (Prevost et al. European J. Cancer, 11, 1589–1592,1993).

The biological activity was tested on rat and human cell lines, namely a GH 3 rat cell line established starting from a pituitary tumor with two 70 and 57 kDa receptors; MCF7 human cell line established starting from a pleural effusion of a breast carcinoma with two main 57 and 42 kDa receptors and human cell line established starting from a small cell carcinoma of the lung with a 57 kDa receptor.

The test was effected on the following compounds of the present invention listed below:

(b)

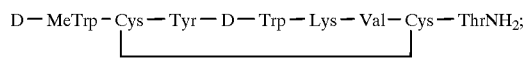

D—MeTrp—Cys—Tyr—D—Trp—Lys—Val—Cys—ThrNH₂;

(c)

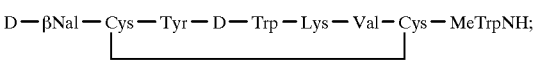

D—βNal—Cys—Tyr—D—Trp—Lys—Val—Cys—MeTrpNH;

(d)

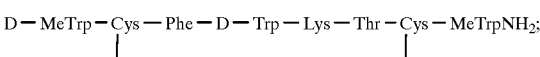

D—MeTrp—Cys—Phe—D—Trp—Lys—Thr—Cys—MeTrpNH₂;

(e)

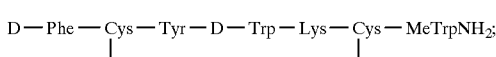

D—Phe—Cys—Tyr—D—Trp—Lys—Cys—MeTrpNH₂;

wherein MeTrp is 2-methyltryptophan, respectively indicated with the letters b, c, d, e.

As a comparison, the known peptides Lanreotide (W. A. Murphy et al. Life Sci. 40, 2515, 1987), Antarelix (R. Deghenghi et al., Biomed. & Pharmacother. 47, 107, 1993) and somatostatin-14 were used.

The pharmacological study of the displacement of the bond between radiolabelled somatostatin and the receptor by the tested peptides showed that the 70 kDa complex corresponds to the 1 or 4 sub-type receptors, the 57 kDa complex corresponds to the sub-type 2 and the 42 kDa complex corresponds to the sub-type 3 or 5.

The tested peptides were suspended in 0.1% acetic acid at the final concentration of 10 mM and stored at 4° C.

Tests were carried out at a $10^{-6}$M concentration.

Auto-radiographies in electrophoresis have shown that the 70 kDa complex is suppressed only by somatostatin-14, whereas the 57 kDa complex is displaced by the peptides according to the invention, by Lanreotide, but not by Antarelix. The 42 kDa complex is suppressed by the peptides c, d, of the invention, which thus prove an action specificity.

Tests with decreasing concentrations, $10^{-6}$, $10^{-7}$, $10^{-8}$M, have shown that the compounds according to the present invention are particularly active compared with the known compounds and somatostatin.

The compounds according to the present invention have inhibitory activity on the release of growth hormone, therefore they are useful as active principles for the preparation of a medicament for the treatment of the diseases characterized by an unbalance of the growth hormone. In particular they are useful for the treatment of endocrine tumors, acromegaly and in the conditions in which the known somatostatin analogues are used.

According to another aspect, the present invention provides cyclic peptides of formula (I) shown above as a support for a radioactive marker, for example $^{125}$Iodine or $^{111}$Indium or $^{99m}$Technetium useful as diagnostic agents for tumors characterized by the presence of somatostatin receptors.

What is claimed is:

1. Compounds of formula (I)

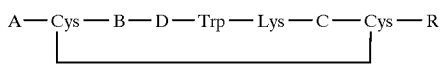

wherein

A is D-AlkTrp, D-β-Nal or D-Phe;
B is Tyr or Phe;
C is Val or Thr;
R is ThrNH$_2$ or AlkTrpNH$_2$;
with at least one of A or R being D-AlkTrp or AlkTrpNH$_2$, respectively;
or the pharmaceutically acceptable salts of said compounds;
wherein AlkTrp is an alkyl group of one to three carbon atoms;
with the proviso that when A is D-β-Nal, B is not Tyr, C is not Val and R is not ThrNH$_2$.

2. Compounds according to claim 1, selected from the group consisting of:

D—MeTrp—Cys—Tyr—D—Trp—Lys—Val—Cys—ThrNH$_2$,

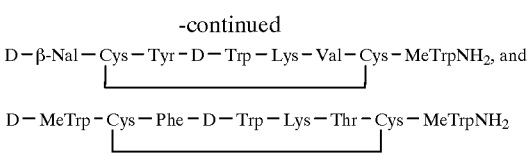

wherein MeTrp is 2-methyltryptophan.

3. A compound according to claim 1, of formula

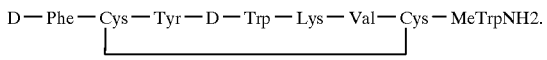

4. Pharmaceutical compounds containing a therapeutically active amount of a compound according to claim 1 in admixture with a carrier and/or pharmaceutically acceptable excipient.

5. A diagnostic agent comprising a compound according to claim 1 in combination with a radioactive marker.

6. Diagnostic agent according to claim 5 wherein the radioactive marker is $^{125}$Iodine, $^{111}$Indium or $^{99m}$Technetium.

7. Compounds according to claim 1, selected from the group consisting of:

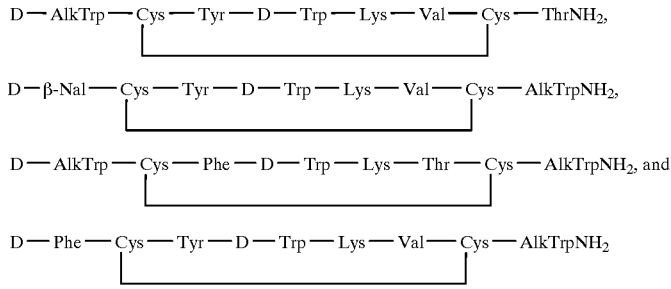

8. Pharmaceutical composition containing a therapeutically active amount of a compound according to claim 7 in admixture with a carrier and/or pharmaceutically acceptable excipient.

* * * * *